United States Patent
Beck

(10) Patent No.: US 8,496,757 B2
(45) Date of Patent: *Jul. 30, 2013

(54) METHOD FOR CLEANING WAFERS USING A POLYCARBOXYLATE SOLUTION

(75) Inventor: Mark Jonathan Beck, Los Gatos, CA (US)

(73) Assignee: Fontana Technology, Campbell, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/555,180

(22) Filed: Jul. 22, 2012

(65) Prior Publication Data

US 2012/0285482 A1  Nov. 15, 2012

Related U.S. Application Data

(63) Continuation of application No. 12/330,486, filed on Dec. 8, 2008, now Pat. No. 8,226,773.

(51) Int. Cl.
*C11D 3/37* (2006.01)

(52) U.S. Cl.
USPC .......... 134/2; 134/26; 134/29; 510/165; 510/166; 510/167; 510/168; 510/170; 510/175; 510/423; 510/434; 510/476; 510/499; 510/504

(58) Field of Classification Search
USPC .......... 134/2, 26, 29; 510/165–168, 170, 510/175, 423, 434, 476, 499, 504
See application file for complete search history.

(56) References Cited

U.S. PATENT DOCUMENTS

| | | | |
|---|---|---|---|
| 5,968,280 A | 10/1999 | Ronay | |
| 7,959,739 B2 * | 6/2011 | Beck | 134/2 |
| 8,084,406 B2 | 12/2011 | Mui et al. | |
| 8,226,773 B2 * | 7/2012 | Beck | 134/2 |
| 2007/0190770 A1 | 8/2007 | Kurashima et al. | |
| 2009/0056744 A1 * | 3/2009 | Carswell | 134/1.3 |
| 2009/0312219 A1 | 12/2009 | Tamura et al. | |

FOREIGN PATENT DOCUMENTS

| | | |
|---|---|---|
| JP | 05-198546 A | 8/1993 |
| WO | 92/06160 A1 | 4/1992 |
| WO | 01/96516 A1 | 12/2001 |
| WO | 2007/076922 A1 | 7/2007 |
| WO | 2007/078955 A2 | 7/2007 |
| WO | 2007/116669 A1 | 10/2007 |

OTHER PUBLICATIONS

English Abstract of Japanese Kokai Publication No. 05-198546, Cleaning Solution for Semiconductor Substrate, Patent Abstracts of Japan, publication date Aug. 8, 1993.

* cited by examiner

*Primary Examiner* — Michael Barr
*Assistant Examiner* — Caitlin N Dunlap
(74) *Attorney, Agent, or Firm* — Donald J. Pagel

(57) ABSTRACT

A cleaning solution and method for removing submicron particles from the surface and/or the bevel of an electronic substrate such as a semiconductor wafer. The cleaning solution comprises a polycarboxylate polymer or an ethoxylated polyamine. The method comprises the step of contacting a surface of the substrate with a cleaning solution comprised of a polycarboxylate polymer or an ethoxylated polyamine. Additional optional steps in the method include applying acoustic energy to the cleaning solution and/or rinsing the surface with a rinsing solution with or without the application of acoustic energy to the rinsing solution.

8 Claims, 4 Drawing Sheets

METHOD FOR CLEANING WAFERS USING A POLYCARBOXYLATE SOLUTION

This application claims the benefit of U.S. patent application Ser. No. 12/330,486, filed Dec. 8, 2008, which is incorporated herein by reference.

BACKGROUND OF THE INVENTION

The manufacturing of devices on semiconductor wafers consists of various repetitive steps, such as deposition of layers, etching of layers, polishing of layers, deposition and photolithography of photoresist layers and so on. After some of these steps, and when various parts or structures of the final device on the wafer are exposed, the semiconductor wafers need to be cleaned to remove particles which may have deposited during such various processing steps and before the next layer is deposited. As presently practiced, particle removal is usually achieved by a combination of mechanical and chemical mechanisms. In many wafer fabs, special dedicated tools are being used to scrub or remove particles, often called scrubbers. In many such scrubbers a mechanical particle removal method is used simply with room temperature or sometimes-heated DI (deionized) water. Chemicals can be added to enhance the removal efficiency. Cleaning tools differ from scrubbers in that mechanical removal techniques are combined with chemicals instead of simple DI water to remove particles both with a mechanical method and a chemical method combined. Additionally in a cleaning tool, other functions can also be performed in addition to particle removal. E.g. removal of metallic impurities, organic impurities and even wet etching of $Si_3N_4$, $SiO_2$, poly-Si, Ni, Co, Ti, TiN or other layers and wet stripping of photoresist can be performed in a cleaning tool in addition to the particle removal function that is the object of this invention.

In a cleaning tool for semiconductor wafers, the most popular combination to remove particles is a combination of megasonics vibration together with a liquid mixture of $NH_4OH$, $H_2O_2$ and $H_2O$ in which the wafers are immersed or with which the wafers are covered. The megasonics systems commonly used in the semiconductor industry use frequencies close to or about 1 MHz (one megahertz).

Before the invention of megasonics, ultrasonics was used. Ultrasonics has frequencies in the range of 20 kHz to about 120 kHz. However, since the invention of megasonics, ultrasonics is rarely used on semiconductor substrates because of the damage potential at frequencies in the range of 20 kHz to about 120 kHz. Hence, megasonics with frequencies close to or about 1 MHz is the current state of the art for semiconductor substrates.

The most popular chemistry conditions used for particle removal together with megasonics on semiconductor wafers, a liquid mixture of $NH_4OH$, $H_2O_2$ and $H_2O$, is a part of the so called RCA cleaning sequence originally developed by W. A. Kern and D. A. Puotinen, at the RCA company in 1965, and published in 1970, RCA Rev., 31, pp. 187-206 (1970). The traditional RCA cleaning sequence consists of 2 steps, the SC-1 step (Standard Clean-1 step) and the SC-2 step (Standard Clean-2 step). Specifically, the particle removal function of this RCA sequence is carried out by the SC-1 step of the RCA cleaning cycle. The SC-1 is also sometimes called the APM (Ammonia Peroxide Mixture) step. The SC-1 step (Standard Clean-1) is mainly aimed at removing particles while the SC-2 step (Standard Clean-2) is mainly aimed at removing metallic contamination. The SC-1 step consists originally of a 1/1/5 mixture of $NH_4OH$ (28-30% strength as $NH_3$-w)/$H_2O_2$ (29-31% strength as $H_2O_2$-w)/DI (De Ionized) water at 70° C. There have been many variations on this recipe both in terms of mixing ratios and in terms of temperature.

Because of the importance of this particle removal step in the semiconductor industry, there has been a lot of research on the mechanism of this particle removal step. This chemistry can even be used without mechanical particle removal mechanism added. It is now widely accepted that, in case when there is no mechanical particle method added to the chemistry, and therefore, when particle removal is achieved by chemical contacting only, then the contacting chemistry simply removes particles due to underetching of the particle. A particular good publication on this mechanism was written by Hiroyuki Kawahara, K. Yoneda, I. Murozono and T. Tokokoro, "Removal of Particles on Si Wafers in SC-1 solution", IEICE Trans. Electron., Vol. E77-C, No. 3, March 1994, p. 492. The underetching theory goes as follows: a controlled amount of the surface layer is uniformly removed or etched all over the surface of the wafer to be cleaned. When etching this surface layer, the material underneath the particle is also etched away and this etching releases the particle from the surface. Then, the particle is washed away.

Since the current state of the art for removing particles by chemical means only, relies on undercut etching, and since etching increases with temperature, everyone so far has found that particle removal efficiency increases with temperature. M. Meuris et al., Microcontamination, May 1992, p. 31, e.g. showed the effect of temperature on etching rate. Therefore, SC-1 solutions are usually used at elevated temperatures. Increased etching can also be achieved by using higher chemical concentration. If the etching is too excessive for the device or substrate at hand, then sometimes the temperature is lowered, but the particle removal efficiency is then reduced as well.

In the prior art, when SC-1 solutions are used without any mechanical particle removal method, i.e. by chemical contacting alone, the temperatures used always range from room temperature up to about 80° C. If there is no reliance on the chemical undercutting and when relying on a mechanical method to remove particles instead, then the high temperature is not needed. For example, when using SC-1 together with megasonics to remove particles, the SC-1 or any alternative high pH chemistry, merely serves to prevent particles from re-depositing. When using megasonics, the particles are removed by the megasonics vibration through the formation of cavitation events and are prevented from reattaching to the surface by the high pH of the SC-1 chemistry or alternative high pH chemistry.

Since megasonics relies on cavitation to remove particles and since cavitation is not very much temperature dependent, but very dependent on the dissolved gases, it has been found that megasonics and SC-1 combined don't remove any particles when there are no gases present. It is possible to create cavitation without any dissolved gases present, so called vacuum cavitation, but this is only possible at very high power levels. Hence, at normal power levels, typically 10-100 W, there is no gaseous cavitation when there are no dissolved gases present and hence there is virtually no particle removal efficiency when using megasonics without any gases dissolved. In R. Gouk, J. Blocking, S. Verhaverbeke, "Effects of Cavitation and Dissolved Gas Content on Particle Removal in Single Wafer Wet Processing", in Proceedings of Semiconductor Pure Water and Chemicals Conference (SPWCC) 2004, Santa Clara, Calif., 2004, it is shown that at 925 kHz and for power levels up to 0.15 W/$cm^2$ (corresponding to 100 W on a 300 mm wafer), there is absolutely no particle removal efficiency for dissolved gas levels of 30 ppb $O_2$. Only for power levels starting at 0.3 W/$cm^2$ (200 W), the particle removal efficiency starts to become non-zero (20%). However, even at only 100 W and with 300 ppb of dissolved gas ($O_2$ in this case), the particle removal efficiency is 90%. This shows clearly the effect of dissolved gas on the particle removal efficiency due to the cavitation of dissolved gas bubbles.

Currently, a cleaning paradox has emerged. Megasonics vibration works well for removing particles and with a very wide temperature range, but the cavitation which the megasonics produces, and which is used to remove particles, also damages the fine patterns on the wafers. Indeed, the patterns on the wafer are becoming so small that they are very to fragile and are very prone to mechanical damage. This started to be a problem when the pattern size on the wafers decreased to a size smaller than 0.3 µm in width or at least in 1 dimension. Initially it was addressed by lowering the megasonics power, but now with pattern sizes sometimes as small as 22 nm in 1 dimension, any megasonics power or rather any cavitation will destroy such patterns.

Therefore, a new method for removing small particles from the front side of the wafer without damaging the fragile structures is necessary. The underetching mechanism, which does not damage the fragile structures, however can also not be used anymore, since the devices are so small, that underetching would remove valuable material from the surface of the device and hence the device characteristics would be degraded. This is the current cleaning paradox that we are faced with.

This is the case, because the current generations of small devices have the active device region extremely close to the top surface. This is very clearly shown for the case of semiconductor wafers and devices made on such wafers, in the publication by F. Arnaud, H. Bernard, A. Beverina, E. El-Frahane, B. Duriez, K. Barla and D. Levy, "Advanced Surface Cleaning Strategy for 65 nm CMOS device Performance Enhancement", Solid State Phenomena Vols. 103-104 (April 2005) pp. 37-40. In this publication, F. Arnaud et al. clearly show that reducing the underetching enhances the transistor characteristics.

Hence the paradox: mechanical particle removal cannot be used anymore for small particle removal, since it also damages the fine patterns, and conventional chemical particle removal by underetching cannot be used anymore, because of loss of surface material which is now a substantial part of the device.

Even in those cases where the substrate is completely flat and where damage is not a paramount concern, it has been found that for very small particles, the mechanical methods are not effective anymore. This is shown in G. Vereecke, F. Holsteyns, S. Arnauts, S. Beckx, P. Jaenen, K. Kenis, M. Lismont, M. Lux, R. Vos, J. Snow and P. W. Mertens, "Evaluation of Megasonic Cleaning for sub-90 nm Technologies", Solid State Phenomena Vols. 103-104 (2005) pp. 141-146. Mechanical methods to remove particles, such as, but not limited to, brush scrubbing, spray aerosol bombardment, and ultrasonic and megasonic vibration, are very effective for the large particles, i.e. for particles >90 nm, but loose efficiency for the very small particles, <90 nm. Hence, there is a need for an improved chemical method to remove these very small particles even on substrates without exposed patterns. This is true for wafers with devices on them after CMP (Chemical Mechanical Polishing). Indeed, these wafers contain parts of the device already on them, but have been flattened or polished without removing all of the layers in order to make it easier for photolithography to pattern the next layer. On such wafers, very small particles are difficult to be removed with conventional mechanical techniques. Gross etching on such polished wafers is not possible, since then the layers which are exposed would be etched away. These layers will become part of the device later and cannot be etched substantially.

As a summary, there is a great need in the semiconductor industry for a solution and a method and an apparatus that can remove small particles from the front side or back side of semiconductor wafers without damaging the fine patterns and without substantial underetching of the surface material. There is a general need for an improved chemical method to remove very small particles (<90 nm) even on substrates without pattern such as wafers with partial devices after chemical mechanical polishing.

More generally, none of the presently known methods can remove efficiently very small particles, since most of the mechanical techniques loose efficiency for small particles and most of the currently known chemical methods are not very effective for very small particles. The prior art does not provide for an improved chemical method to remove very small particles more efficiently than the ubiquitous SC1 solution for wafers with partial structures or layers on them.

BRIEF SUMMARY OF THE INVENTION

Briefly, the present invention is a method and cleaning solution for cleaning an electronic substrate, such as a semiconductor wafer, as part of the device manufacturing process. The method comprises the steps of contacting a surface of the electronic substrate that has partial structures or patterns (electronic structures) of a device exposed with a cleaning solution comprised of a polycarboxylate polymer, ethoxylated polyamine or an ethoxylated quaternized diamine; and then removing the cleaning solution from the surface. Additional optional steps in the method include applying acoustic energy to the cleaning solution and following the cleaning by rinsing the surface with a rinsing solution with or to without the application of acoustic energy to the rinsing solution.

The cleaning solution of this invention for removing submicron particles from the surface and/or the bevel of an electronic substrate such as a wafer with partial device structures or patterns contains a polycarboxylate polymer, ethoxylated polyamine or an ethoxylated quaternized diamine. The polycarboxylate polymer of the present invention comprises homopolymers or copolymers of acrylic acid, methacrylic acid, maleic acid, fumaric acid, itaconic acid, and the like.

The cleaning solution which either contains a concentrated polycarboxylate polymer or a concentrated ethoxylated polyamine or both and may also additionally contain a base or an acid, can be delivered in concentrated form and then diluted at point of use and then dispensed or contacted on the surface or the bevel of an electronic substrate such as a wafer as part of the manufacturing of devices on such wafers. The dispensing and/or cleaning and/or rinsing optionally can be carried out at subambient temperatures. A base such as ammonium hydroxide, tetramethylammonium hydroxide, choline can be added and in addition or alternatively, an amine such as monoethanolamine and a biocide can be added. Alternatively or in addition, a surfactant and/or a sequestering agent can be added.

After dilution or even undiluted, any of the cleaning solutions of the invention can be used in a method to clean the surface of an electronic substrate such as a wafer as part of the manufacturing of devices on such wafer.

The cleaning solution can also be used to clean the bevel of the electronic substrate such as a wafer. The bevel can be cleaned with e.g. a brush or a megasonic nozzle together with the solution of this invention.

After cleaning the surface or the bevel with any of the cleaning solutions of this invention, the cleaning solution needs to be rinsed from the wafer and/or bevel surface. The rinsing step can also be assisted with a spray or with megasonics, without causing damaging cavitation if fragile structures are present on the surface. The damaging cavitation can be avoided by either not using dissolved gas or by using high frequency megasonics.

BRIEF DESCRIPTION OF THE SEVERAL VIEWS OF THE DRAWING

The invention is best understood from the following detailed description when read in connection with the accompanying drawings. It is emphasized that, according to common practice, the various features of the drawing are not to scale. On the contrary, the dimensions of the various features are arbitrarily expanded or reduced for clarity. Included are the following figures.

DETAILED DESCRIPTION OF THE INVENTION

Figure 1:
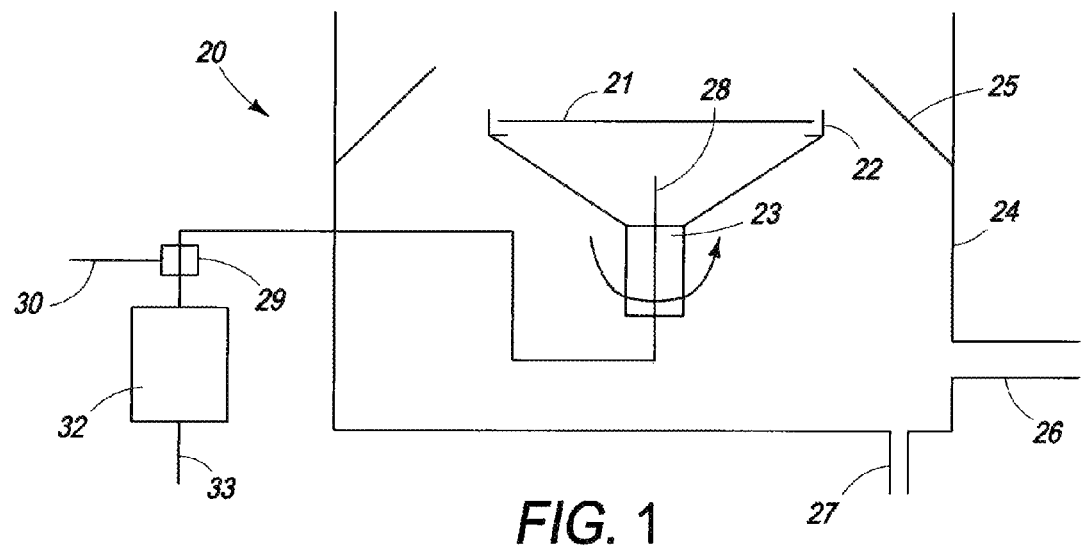
FIG. 1 is a schematic diagram of a single wafer spin-spray system according to the present invention for removing small particles from the front side of the wafer.

A cleaning solution used in the present invention comprises a polycarboxylate polymer solution. In one embodiment, the polycarboxylate polymers may comprise homopolymers or copolymers of acrylic acid, methacrylic acid, maleic acid, fumaric acid, itaconic acid and the like. When the term homopolymer is used, it is intended that it includes by definition, polymers that may contain quantities of about 20 mole percent or less, of one or more comonomers. In other words, a polymer containing up to 20 mole percent of comonomers will still be considered a homopolymer. The cleaning solution may also comprise a blend of the above polycarboxylate polymers.

Particularly suitable polycarboxylate polymers are prepared from monomers having the general formula (Formula 1):

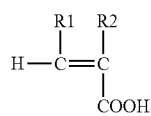

Where R1 and R2 is either a hydrogen atom (H) or methyl radical ($CH_3$, also represented by Me).

A polycarboxylate polymer (homopolymer) formed from monomers of this type can be schematically represented by the following formula (Formula 2):

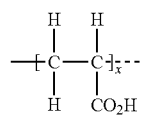

where R1 may be H or COOH (carboxyl); and R2 may be H, Me or $CH_2COOH$.

In specific embodiments, the monomer may be acrylic acid (R1 and R2 are H) or methacrylic acid (R1=H and R2=Me). In other embodiments, the monomers may be maleic acid (R1=COOH and R2=H, with the carboxylic acid groups in the cis configuration); fumaric acid (R1=COOH and R2=H, with the carboxylic acid groups in the trans configuration); and itaconic acid (R1=H and R2=$CH_2COOH$). Polycarboxylate polymers (copolymers) comprising combinations of these monomer units may also be used (e.g. Formula 5, below).

Other suitable polymers are a maleic/olefin copolymer. This embodiment of the polycarboxylate polymer comprises a copolymer derived from maleic anhydride and a lower olefin. Preferably the maleic anhydride monomer has the following formula (Formula 3):

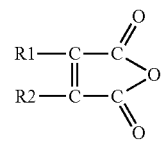

where R1 and R2 are independently H, an alkyl or a phenyl group. Most preferably R1 and R2 are H. The lower olefin component is e.g. ethylene, propylene, isopropylene, butylene or isobutylene and most preferably ethylene. This maleic/olefin copolymer can be added to a suitable acrylic acid or methacrylic acid homopolymer or copolymer. The maleic/olefin copolymer has the formula (Formula 4):

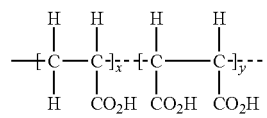

Other suitable polycarboxylate polymers are polymaleic acids, i.e. homopolymers of maleic acid. Still other suitable polycarboxylate polymers are acrylic acid/maleic acid copolymers which can be represented schematically by the following formula (Formula 5):

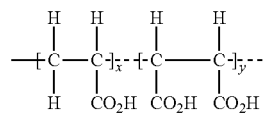

Formula 5 is a copolymer of polyacrylates and polymaleates. In the schematic representation above, the first group is an acrylate group and the second group is a maleate group.

An acrylic homopolymer can be schematically represented by the following structure (Formula 6):

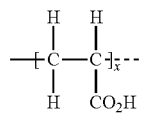

The average molecular weight of the polycarboxylate polymers given by Formulas 1-6 can vary between 300 and 1000000 Dalton. Preferably the average molecular weight is between 500 and 200000, even more preferably between 1000 and 80000 and most preferably between 2000 and 10000.

A particularly good copolymer for use in the present invention is a 50/50 acrylic/maleic copolymer (Formula 5) with an average molecular weight of about 3000 Dalton.

Such an acrylic acid/maleic acid copolymer or an acrylic homopolymer or a polycarboxylate polymer in general is typically synthesized by a raw material supplier and is typically made available in either the acid form or in a neutral form where the acid carboxylic groups are neutralized by a cation, most often $Na^+$ (sodium). The acid form is preferable to use as the starting raw material for the cleaning solution blend. In the above schematic representations of the polymers, typically the acid form is shown. For the $Na^+$ neutralized form, the $CO_2H$ group in the formula above should be replaced by a $CO_2Na$ group.

For the cleaning solution of this invention, water soluble salts of carboxylic polymers as described above are especially preferred. Alternatively an ester of the carboxylic polymers can be used. The water soluble salt can be preferably an ammonium or substituted (quaternary) ammonium salt. For semiconductor wafer cleaning, an alkali free soluble salt is preferred. The carboxylic polymers are converted to the desired salt by reaction of the acid form with the appropriate base. A typical alkali free soluble salt can be made by reaction of the polymer in the acid form with e.g. ammonium hydroxide, tetramethylammonium hydroxide or choline. Alternatively the ester form can be reacted with the appropriate base.

Typically the polycarboxylate polymer of this invention is added to a base in concentrated form at the chemical solution blending plant. Most often the base will be $NH_4OH$ for semiconductor cleaning, but it can also be TMAH (Tetra Methyl Ammonium Hydroxide) or choline or any other base that is suitable for the semiconductor cleaning operation. For semiconductor wafer cleaning, this concentrated base solution with the polycarboxylate polymer can be used as a direct replacement for the $NH_4OH$ in the ubiquitous SC1 solution. This concentrated solution is then typically shipped to the manufacturing plant where the cleaning operation will be performed. At this manufacturing plant, the concentrated solution will be diluted with $H_2O$ and or other chemicals to make up the cleaning solution. However, the polycarboxylate polymer can also be shipped in the acid form and then the base gets added at the semiconductor cleaning plant.

Alternatively to the polycarboxylate polymers, an ethoxylated polyamine can be used in a cleaning solution to remove particles. Schematically, an ethoxylated polyamine for use according to this invention has the following general formula (Formula 7):

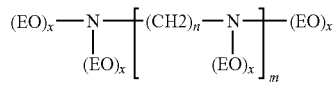

where EO is the oxyethylene moiety ($-CH_2CH_2O-$). The preferred ranges are as follows: the value of x ranges from 1 to 100, the value of n ranges from 1 to 30 and the value of m ranges from 1 to 30. The last EO is typically terminated with H (not shown in the schematic formula). A particular useful ethoxylated polyamine is the ethoxylated pentamine where x=15, n=2 and m=4. Schematically, the structure of the ethoxylated pentamine, which is very useful for the current invention, is as follows (Formula 8):

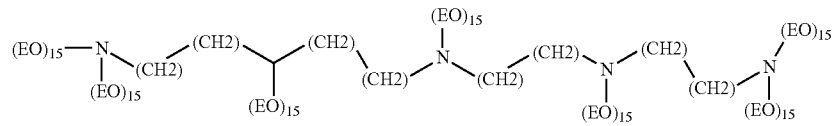

Another useful compound for use in the current invention is the ethoxylated, quaternized diamine with the following structure (Formula 9):

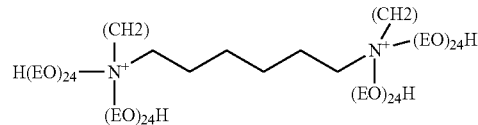

The ethoxylated polyamine of this invention will typically be added in concentrated form to make up a chemical solution in the blending plant. Typically the ethoxylated polyamine will be blended into either a neutral solution or an acidic solution.

Both the polycarboxylate polymer solution and the ethoxylated polyamine can be supplied as a concentrated solution without base. However, when using the polycarboxylate polymer solution for cleaning semiconductor wafers, the final blended cleaning solution is typically used at alkaline pH values, preferably in excess of pH 8. Ammonium hydroxide or other bases are typically added to increase the pH of the solution. This can be done at the chemical manufacturing or blending plant, but it can also be done at point-of-use. The ethoxylated polyamine on the other hand can be used over a wide pH range and is not limited to alkaline pH cleaning when using this for cleaning semiconductor wafers. Finally, Surfactants and chelating agents can also be added.

In addition, in order to make up a cleaning solution for semiconductor wafers, $H_2O_2$ can be added to make an analogue of the omnipresent SC-1 solution. The addition of $H_2O_2$ is useful to avoid any Si surface etching on such wafers, as is known in the prior art. The $H_2O_2$ preferably is added at point-of-use, whereas the other components can be blended together at the chemical blending plant.

The ammonium hydroxide with the polycarboxylate polymer with or without peroxide added is a superior cleaning solution to the conventional ammonium hydroxide and peroxide solution for wafers with partial structures, layers or patterns to make finished devices on such wafers. It can remove very small particles <90 nm and can remove particles even without any mechanical removal technique added. This is very important for wafers which have fragile structures exposed to the cleaning solution.

After dilution of the source solution in the fab for cleaning use, the final concentration of the polycarboxylate polymer in the cleaning solution for cleaning the substrates is preferably between 0.001%-6% by weight. More preferably the concentration of the polycarboxylate polymer in the cleaning solution is between 0.01% and 2% and most preferably the polycarboxylate polymer in the cleaning solution is between 0.1% and 1% by weight. A particular good and effective concentration is about 0.6% for fast particle removal, but the cleaning effect of the polycarboxylate polymer on semiconductor wafers can even be observed down to 0.001%. There is a trade-off between concentration and cleaning time. At lower concentration the cleaning effect of the polycarboxylate polymer can be observed at longer cleaning times, whereas at higher concentration, even for short contacting times, the cleaning effect is already clearly seen.

When using the ethoxylated polyamine for cleaning semiconductor wafers, the concentration ranges for the ethoxylated polyamine are preferably at concentrations between 0.001% and 5% and more preferably between 0.01% and 2% ad most preferably between 0.1% and 1% by weight.

Typically, the polycarboxylate polymer or the ethoxylated polyamine can be supplied to the fab in a concentrated solution, which can then be diluted with DI water and with other chemicals at point-of-use or centrally in the fab to yield the final cleaning concentration. The polycarboxylate polymer in a concentrated source solution can be supplied close to its solubility limit in such a source solution in order to reduce transportation expenses, but substantially lower concentrations can be used as well e.g. to suppress raw material costs and hence to reduce the final sales price of the blended chemical. Other reasons to supply a lower concentration is e.g. if the fab is using equipment that is set up for diluting the source concentration in a pre-fixed dilution ratio. E.g. typical dilution ratios used in fabs are 5 times such as used e.g. in a 5:1:1 SC-1 bath. In that case, the polycarboxylate polymer concentration, when supplied together with the $NH_4OH$ in 1 solution, will need to be substantially lower in the source solution in order to give the right concentration after diluting according to such a pre-fixed ratio. Alternatively, the fab may not be set up to handle any dilution and will require the cleaning solution supplied at the use concentration. The solubility of the polycarboxylate polymer depends on its molecular weight. For this invention, polycarboxylate polymers with a molecular weight between 300 and 1,000,000 Daltons can be used. Higher molecular weight polycarboxylate polymers will be less soluble than lower molecular weight polycarboxylate polymers. Average molecular weight numbers (3000-70,000 Daltons) will typically have a solubility of about 40-60%-w in water. Therefore generally the solution can be supplied to the fab in-concentrations ranging anywhere from 0.001% to 60%.

Ethoxylated polyamines are substantially less soluble. The ethoxylated pentamine e.g. has a solubility of around 5%-w in water.

Typically the source solution as supplied by the chemical blending operation will be used in the fab for cleaning either straight (i.e. undiluted), or diluted, but diluted with water and/or other chemicals is preferable for economic reasons. It is clear that transporting a concentrated solution and diluting it at point-of-use with local DI water is more economical than diluting at the chemical blending company and then transporting the diluted solution over long distances.

When diluting the source solution, dilution ratios will be preferably between 5 and 10,000 times with DI water to make up the substrate cleaning solution, more preferably 5 to 1000 times, and most preferably 5 to 100 times. Besides dilution with water, other chemicals can be added as well.

When ammonium hydroxide is added to the concentrated source solution to make a source solution containing polycarboxylate polymer and ammonium hydroxide, it can be added in a concentration range of 1%-28%-w (weight of $NH_3$) to make a source solution consisting of ammonium hydroxide and polycarboxylate polymer. This then can easily replace the now commonly used ammonium hydroxide source solution in fabs to clean wafers with the common SC-1 solution. But any other suitable base can be used instead of ammonium hydroxide for making up the source solution.

The source solution may also contain from 0.01% to 40% of an organic amine. Suitable organic amine compounds may be selected from alkanolamines (e.g. primary alkanolamines: monoethanolamine, monoisopropanolamine, diethylethanolamine, ethyl diethanolamine, secondary alkanolamines: diethanolamine, diisopropanolamine, 2-(methylamineo) ethano, morpholine, ternary alkanolamines: triethanolamine, tri-isopropylamine), alkylamines (e.g. primary alkylamines, monomethylamine, monoethylamine, monopropylamine, monobutylamine, monopentylamine, cyclohexylamine, secondary alkylamines: dimethylamine), alkyleneamines (e.g. primary alkylene amines: ethylenediamine, propylenediamine, triethylenetetramine), and mixtures thereof. Preferred examples of such materials include monoethanolamine, ethylenediamine, triethylenetetramine and mixtures thereof. The most preferred is monoethanolamine. The amount of the organic amine preferably ranges from 0.01% to 20%, and most preferably from 0.2% to 2%.

The source solution may also contain a biocide such as 2-Methyl-4-isothiazolin-3-one (MIT) or 2-Methyl-4-Isothiazolin-3-one Hydrochloric acid (C4H4NOS, HCl), (MIHCA). The concentration of the biocide is preferably from 1 ppm to 100 ppm, and more preferably form 30-70 ppm. Other biocides may be used as well. Biocides do not improve the particle removal efficiency but prevent any bacterial growth in the chemicals.

Surfactants can also be added. Typically non-ionic surfactants are preferred. Preferred surfactants are the ethylene oxide type surfactants with a general structure $C_nH_{2n+1}O(C_2H_4O)_mH$. A typical non-ionic surfactant is $C_{12}H_{25}O(C_2H_4O)_{11}H$. The concentration of the surfactant in the concentrated source solution will be preferably between to 0.1% and 5%. Most preferably concentrations are around 0.5% for the concentrated source solution. The concentration after dilution with water and when used for cleaning the surfaces will be preferably between 0.0001 to 0.5% by weight. This is between 1 ppm and 5000 ppm by weight. More preferably the concentration after dilution will be between 10 ppm and 500 ppm. Surfactants do not substantially improve the particle removal efficiency, but may be added for other reasons, such as for wetting purposes when the surface is hydrophobic.

Sequestering agents or complexing agents can also be added. Sequestering agents do not substantially improve the particle removal efficiency, but can be added to prevent metallic impurity deposition on the wafer surface. Preferred sequestering or complexing or chelating agents arc the nitrogen-containing carboxylic acids such as ethylenediaminetetraacetic acid (EDTA) and diethylenetriaminepentaacetic acid (DTPA). The concentration of the sequestering agent after dilution with water and when used for cleaning the surfaces will be preferably between 10 ppm and 500 ppm.

The solutions of this invention with polycarboxylate polymers remove particles substantially better than the conventional ammonium hydroxide only solutions, such as the ubiquitous SC1 solution or other solutions known in the prior art for cleaning wafers with partial structures or patterns of devices on them.

The solution with polycarboxylate polymers or ethoxylated polyamines with or without amines, surfactants and or sequestering agents and other chemicals added can be contacted on the substrate of the wafer in a bath or immersion type apparatus, which can be single substrate or batch, or in a spinning wafer type apparatus, which can also be single substrate or batch or in a horizontal conveyor belt style apparatus or in any other apparatus type suitable for contacting one or more substrates with a solution with polycarboxylate polymers or ethoxylated polyamines with or without $NH_4OH$ or other chemicals added and with or without amines, surfactants and or sequestering agents added.

Finally, it is clear that other substances may be added to the solution with polycarboxylate polymers with or without $NH_4OH$ or any other base. Adding other substances to this solution does not constitute a deviation from the idea of the current invention. Specifically $H_2O_2$ may be added to the solution.

The removal efficiency of more tenaciously adhered particles on the surface can be improved from the simple contacting with a polycarboxylate polymer or ethoxylated to polyamine containing solution of this invention in several ways.

Such known additional ways include, for example, megasonics, an aerosol spray and a scrubbing action with a PVA brush. Indeed, the megasonics act by causing cavitation events due to the dissolved gases in the solution. These cavitation events cause a mechanical agitation on the adhered particles and hence dislodge them from the surface of the wafer. The megasonics also act by reducing the boundary layer. An aerosol spray technique exerts a mechanical force onto adhered particles by causing a very fast flow of liquid over the surface of the wafer. An aerosol spray technique can be set up such that it only exerts a force on large particles and large features. Hence, an aerosol spray technique can be selective for exerting a force on large particles and large features, but not on small particles and small features, which are very fragile. An aerosol spray technique also reduces the boundary layer in a similar way like the megasonics.

In addition, after the cleaning is finished, it is advantageous to follow up the cleaning sequence with an improved DI water rinse. The improved DI water rinse can consist of a megasonics without gas to avoid cavitation or a megasonics at high frequency. The improved DI water rinse can also be a rinse with a spray. A spray rinse can be a regular water spray or an aerosol spray. A regular water spray is effective at high flows; typically a flow in excess of 1 L/min for a 300 mm sized substrate such as a semiconductor wafer is very effective.

The temperature of the cleaning solution during cleaning of wafers can be any temperature from 0 degrees C. to 100 degrees C. with room temperature preferred because of its ease and economical advantage. For absolute best particle performance lower temperatures are even preferred. Preferred temperatures for best particle performance are between 1 degrees C. and 20 degrees C. and more preferred from 3 degrees C. to 15 degrees C. and most preferred from 5 degrees C. to 12 degrees C. Lower temperatures are also advantageous to reduce the surface etching amount, which is often undesirable as it removes active material from semiconductor structures, part of the devices present on the wafers. At lower temperatures a higher pH can be used with equivalent etching amount as one would have at a higher temperature, but at a considerable lower pH. The higher pH is improving the cleaning performance. The subsequent rinsing can also be carried out at subambient temperatures to improve the particle performance.

After cleaning with the solution of the current invention containing either a polycarboxylate polymer or an ethoxylated polyamine, it is desirable to remove all of the polycarboxylate polymers, or all of the ethoxylated polyamines. Normally this can be done adequately by thorough rinsing. If absolutely the lowest levels of remains are necessary, especially after using the polycarboxylate polymer solutions, then a two stage cleaning can be used. The first stage is a $NH_4OH$ based clean, such as an SC-1, or simply an $NH_4OH$ based rinsing. The second stage is an HCl based cleaning, such as SC-2, or simply HCl rinse water can be used. Alternatively the $NH_4OH$ based step can be skipped and the rinsing can be acidified with HCl. This is particularly useful for the ethoxylated polyamine solutions.

For purposes of illustration, the principles and methods of the present invention for a concentrated solution and a cleaning solution and a method and apparatus for cleaning the front side of the wafer and/or the back side of the wafer and/or the bevel of the wafer will now be described.

A typical make-up of a concentrated source solution according to the invention for use in a 5:1:1 SC-1 solution and when the copolymer is supplied together with the $NH_4OH$ as one blended source solution is shown in Example 1:

|  | Percent (%) |
| --- | --- |
| 50/50 acrylic/maleic copolymer in the acid form with an average molecular weight of 3000 Daltons | 3.5%-w |
| $NH_4OH$ (26%-w as $NH_3$) | Balance |

This concentrated solution can be made off-site and be transported to the fab. In the fab, it is typically diluted with water with a factor 5:1:1 $H_2O$:$H_2O_2$(30%):concentrated solution of Example 1 to a final cleaning concentration of 3.7% $NH_4OH$ (as $NH_3$), 0.5% acrylic/maleic copolymer and 4.3% $H_2O_2$. $H_2O_2$ is typically be added in such cleaning solutions in the same or higher amount as $NH_4OH$. It has to be remarked that the pH of these final solutions will be slightly less than what would be obtained without the 50/50 acrylic/maleic copolymer (in the acid form) since the 50/50 acrylic/maleic copolymer contains acidic carboxylic groups. One can compensate for that by using the appropriate slightly higher amount of the source solution to end up with the same final pH as one would have when using a conventional 5:1:1 solution made up of $NH_4OH$:$H_2O_2$:$H_2O$. In the case of a 5:1:1 solution, this difference is however negligible. This compensation is not necessary if the 50/50 acrylic/maleic copolymer would be supplied in a neutral form. The final $NH_4OH$ concentration at 26%-w will be slightly lower than the 28%-w as is more common, when the copolymer will be added already dissolved in water to 28%-w standard solution. When the copolymer will be added in solid form, the 28-w% concentration can be maintained closer.

A typical make-up of a concentrated solution according to the invention for use in a 20:1:1 or a 20:1 solution is shown in Example 2:

|  | Percent (%) |
| --- | --- |
| 50/50 acrylic/maleic copolymer in the acid form with an average molecular weight of 3000 Daltons | 12%-w |
| NH4OH (21%-w as NH3) | Balance |

This concentrated solution of Example 2 can be made off-site and be transported to the fab. In the fab, it is typically diluted with water with a factor 1:20 to a final cleaning concentration of 1% $NH_4OH$ (as $NH_3$) and 0.6% acrylic/maleic copolymer. $H_2O_2$ can also be added. $H_2O_2$ would typically be added in the same or higher amount as $NH_4OH$ to make a 20:1:1 solution $H_2O:H_2O_2$:source solution of Example 2. In this case, due to the acidifying effect of the acrylic/maleic copolymer (when supplied in the acid form), the pH of a 20:1:1 $H_2O:H_2O_2$:source solution of Example 2 is in a similar range as the pH of a 20:1:0.3 solution of $H_2O:H_2O_2:NH_4OH$ (28% $NH_3$). One can compensate for that if desired by decreasing the $H_2O_2$ concentration or by increasing the concentration of the source solution of Example 2.

A typical make-up of a concentrated solution according to the invention for use in a 30:1 or a 30:1:0.22 solution is shown in Example 3:

|  | Percent (%) |
|---|---|
| 50/50 acrylic/maleic copolymer in the acid form with an average molecular weight of 3000 Daltons | 15.6%-w |
| NH4OH (19%-w as NH3) | balance |

This concentrated solution of Example 3 can be made off-site and be transported to the fab. In the fab, it is typically diluted with water with a factor 1:30 to a final cleaning concentration of 0.64% $NH_4OH$ (as $NH_3$) and 0.5% acrylic/maleic copolymer. $H_2O_2$ can also be added. In order to get the same pH as one would get for a 30:1:1 conventional $H_2O$:$NH_4OH(28\%):H_2O_2(30\%)$ solution, $H_2O_2$ would typically be added in the same or higher amount as the free $NH_4OH$ which is not used to neutralize the copolymer, when the copolymer is added in the acid form. That would be the case for a mixing ratio of about 30:1:0.22 or alternatively said a mixing ratio of 136:4.5:1 for $H_2O$:concentrated solution of example 3: $H_2O_2(30\%)$. The concentration of the H2O2 may also be doubled e.g. to roughly a 70:2:1 $H_2O$:concentrated solution of example 3: $H_2O_2$ solution. This will have a pH comparable to a conventional 30:1:2 $H_2O:NH_4OH:H_2O_2$ solution.

A typical make-up of a concentrated solution according to the invention is shown in Example 4:

|  | Percent by volume (%) |
|---|---|
| 50/50 acrylic/maleic copolymer in the acid form with an average molecular weight of 3000 Daltons | 15% |
| TMAH | 5% |
| Water | Balance |

This concentrated solution can be made off-site and be transported to the fab. This solution can be diluted in the fab with water and/or other chemicals. Typically this solution can be used to clean Cu/Low K or in general Cu wafers. Because of the pH of this solution, this solution will grow a thin passivating oxide on Cu. In many cases this is desirable to stop uncontrolled oxidation of metallic Cu.

Typically, pH ranges between 8 and 14 and preferably between 9 and 12 and most preferably between 10 and 11 are very good for cleaning particles in combination with the acrylic/maleic copolymer or the acrylic homopolymer or any polycarboxylate polymer in general. Other substances can be used instead of $NH_4OH$ to get a similar pH. Typical other substances used to increase the pH are e.g. TMAH (as in example 4) and choline.

An example of a single wafer spin-spray cleaning chamber will now be given in more detail. Referring to FIG. 1, the spin chamber 20 contains the wafer 21, being held horizontally by a wafer holder 22, connected to a motor 23. The wafer is held with the front side of the wafer facing down. The motor and wafer holder assembly is mounted in a bowl 24 containing a liquid diverter 25, an exhaust 26 and a drain 27. A nozzle 28 is mounted to direct the liquid solution with the acrylic/maleic copolymer or acrylic homopolymer preferably at ambient or subambient temperature onto the spinning wafer 21. The nozzle 28 is directed to dispense the liquid from below the wafer while the wafer is facing front-side down. In this way, gravity helps in transporting, the particles away from the surface, out of the boundary layer and into the flowing stream. The nozzle 28 is fed from a mixer 29 where a solution of acrylic/maleic copolymer or acrylic homopolymer and $NH_4OH$ and DI water is mixed in the desired ratio. The solution is fed from line 30. The chiller 32 may cool the incoming DI water from line 33 down to a desired subambient temperature. In addition to the nozzle 28, which can supply subambient temperature liquid onto the spinning wafer, another nozzle (not shown) can be used to supply an accelerated atomized aerosol of the solution onto the wafer. This accelerated nozzle helps in bringing the solution in close proximity to the adhered particles on the wafer.

Figure 2:
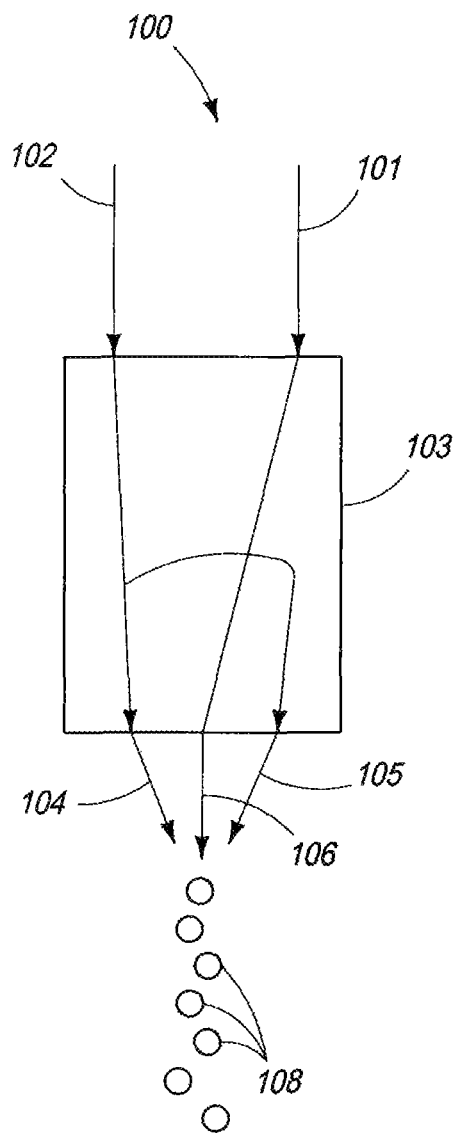
FIG. 2 is a schematic representation of a nozzle where the solution of polycarboxylate polymer or ethoxylated polyamine is accelerated by an $N_2$ or CDA gas flow outside the nozzle body.

A close up of such a accelerated atomized aerosol nozzle configuration is shown in FIG. 2. Referring to FIG. 2, a nozzle 100 is shown with nozzle body 103 and liquid inlet 101 for the solution with acrylic/maleic copolymer or acrylic homopolymer. Inlet 102 is the gas inlet. A variety of accelerating gases can be used, but most conveniently $N_2$ or CDA (Compressed Dry Air) can be used. The liquid inlet 101 is connected to the liquid outlet 106. The gas inlet 102 is connected to gas outlets 104 and 105, which can be a single circular outlet. The gas coming out of outlets 104 and 105 atomizes and accelerates the atomized droplets 108 of the liquid coming out of outlet 106. The atomized aerosol containing acrylic/maleic copolymer or acrylic homopolymer is jetted towards the wafer surface.

Even though the chiller 32 in spin chamber 20 is positioned before the mixer 29, the mixing of acrylic/maleic copolymer or acrylic homopolymer and DI water can be done before the chiller. Even though in FIG. 1, the atomized aerosol is supplied with a solution of acrylic/maleic copolymer or acrylic homopolymer, the aerosol can also be supplied with simple DI water. In this case the aerosol is merely used to create a motion in the solution already on the wafer or the aerosol jet is used to remove large particles selectively as is known in the prior art.

After the wafer contacting with a solution of acrylic/maleic copolymer or acrylic homopolymer, the wafer can preferably be rinsed with subambient temperature DI water. Indeed, the rinsing of the wafer with subambient temperature DI water will reduce the final particle count. The drying can be done with any of the known methods for drying wafers. In batch mode the most preferred drying method is the surface tension gradient method, preferably using a vapor of IPA. However, a spin dry method can also be used. In a single wafer mode a surface tension gradient drying method can be used or a simple spin dry method can be used. Any other method to dry a substrate without adding substantial contamination during the process of drying, i.e. any known clean drying method, can also be used. If a surface tension gradient drying method is used, a vapor of IPA will be blown in the center of the wafer, while the wafer is facing front-side down. This IPA nozzle is not shown in FIG. 1.

Figure 3:
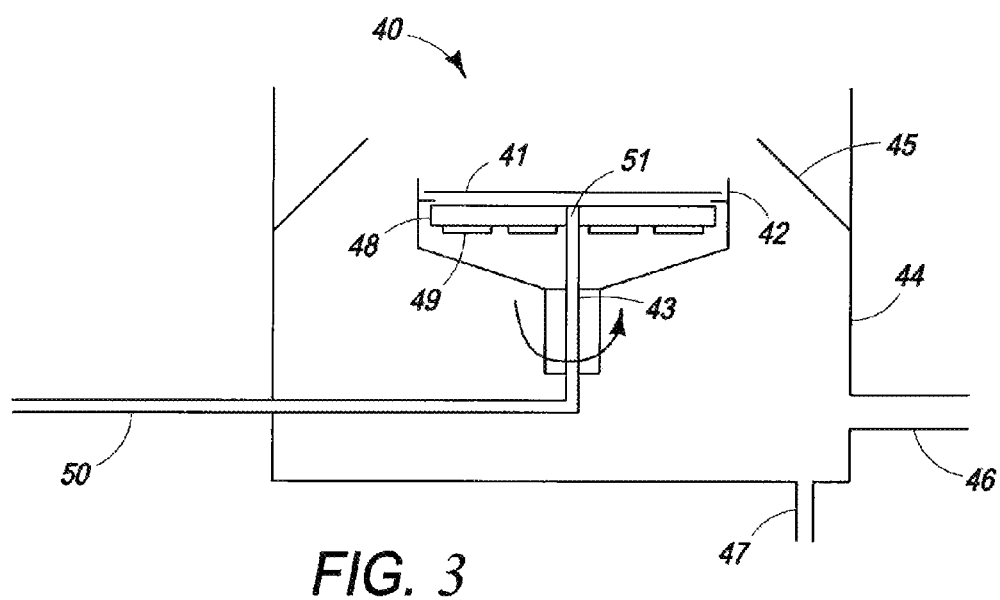
FIG. 3 is a schematic diagram of a single wafer spin-spray system of a preferred embodiment of the present invention for removing small and large particles from the front side of the wafer.

Even though the simple act of contacting the surface of a wafer with a solution of acrylic/maleic copolymer or acrylic homopolymer can remove submicron particles very effectively, the removal efficiency can be improved with an accelerated jet, and it can also be done by the use of megasonics. One such apparatus, a single wafer spin-spray tool, is shown in FIG. 3. In the single wafer spin-spray apparatus 40 of FIG. 3, a wafer holder 42 connected to a motor 43 holds a wafer 41. The wafer can be held with the front side of the wafer facing down. Positioned below the wafer is a sonic transducer 48. The sonic transducer is e.g. made of stainless steel or aluminum and is preferably coated with PFA. On the backside of the sonic transducer, PZT crystals 49 are bonded to generate the sonic waves. The PZT crystals are connected to a megasonic frequency power supply (not shown) and protected in a housing to isolate the PZT crystals from the cleaning liquids (not shown). Closer to the center of the wafer, there is a liquid feed through 51, which is connected to a chemical feed line 50. This chemical feed line supplies chemicals or DI water through the sonic transducer 48 to the backside of the wafer 41. The PZT crystals 49 generate the sonic waves in a frequency range of 200-6000 kHz. Conventionally frequency ranges between 700 kHz and 1.8 MHz are being used. This is commonly used for megasonics cleaning. However, any frequency range of 200-6000 kHz can be used.

Figure 4:
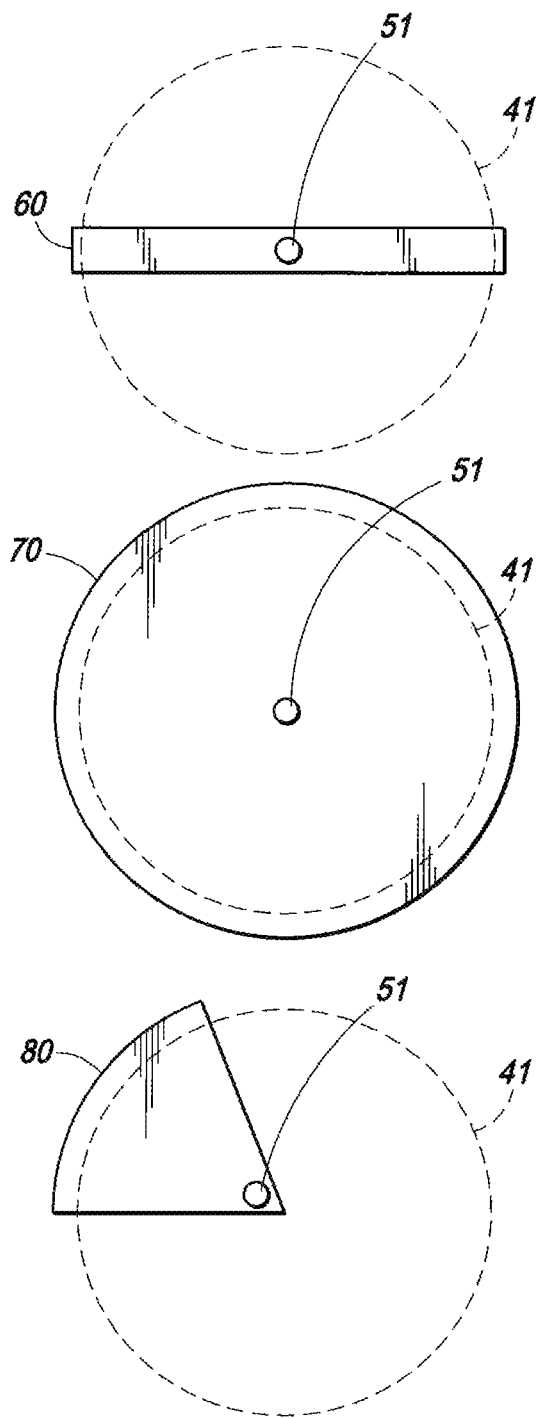
FIG. 4 is a schematic top view of various transducers that can be used in the preferred embodiment shown in FIG. 3, positioned below the wafer.

The wafer 41 with wafer holder 42, motor 43 and sonic transducer 48 is mounted inside a bowl 44 with liquid diverter 45, drain 47 and exhaust 46. The sonic transducer 48 can have various shapes as is shown in FIG. 4. In FIG. 4, a linear transducer 60, a full wafer disk shaped transducer 70 and a pie-shaped transducer 80 are shown. In each transducer 60, 70 and 80, the outline of the wafer 41 is shown and the chemical feed through 51 is shown.

The final rinse method is very important, since the final rinse needs to remove all of the acrylic/maleic copolymer or acrylic homopolymer from the surface. The final rinse method can be preferably carried out with megasonics with or without gas to avoid damage, high frequency to avoid damage. The final rinse can also be carried out with an atomized spray. The final rinse is preferably carried out with subambient temperature water.

In addition, the final rinse with subambient temperature water can be combined with a surface tension gradient particle removal and drying technique. Using an IPA vapor of some sort usually generates the surface tension gradient. The subambient temperature water can be contacted to the front side of the wafer first, followed by a surface tension gradient cleaning and or drying.

The solution of the present invention is very useful for bevel edge cleaning. Indeed, the acrylic/maleic copolymer or acrylic homopolymer is very powerful at removing contamination from the bevel of the wafer. This is best carried out with an aggressive mechanical means that is selective to the bevel itself. The easiest mechanical assist that is selective to the bevel itself is a brush. If the brush material only contacts the wafer bevel edge and not the front side of the wafer, then this method can remove the contamination from the bevel edge without damaging fragile structures on the front side of the wafer. Finally a last mechanical assist is a sonic energy that is confined to the edge of the wafer. The sonic energy will only cause damage when the energy is transferred to the liquid. Hence, the front side of the wafer must be kept dry while applying this sonic energy to the bevel edge of the wafer.

In view of this disclosure, a representative embodiment of the present invention is a method for cleaning submicron particles off a surface of a substrate. The method comprises the step of contacting a surface of the substrate with a cleaning solution comprised of a cleaning agent, such as a polycarboxylate polymer, including the polycarboxylate homopolymers or copolymers described previously with respect to Formulas 1-6, or an ethoxylated polyamine or an ethoxylated quaternized diamine described previously with respect to Formulas 7-9). Generally, the substrate is an electronic substrate meaning that it is a semiconductor wafer, a storage medium, such as a hard disk, or a substrate used in manufacturing wafers or storage media, such as a photomask or an imprint mold, or read/write head assembly parts. The method may be used to clean a single substrate or more than one substrate at a time. An optional step in the method is to apply acoustic energy to the cleaning solution while the cleaning solution is in contact with the surface. Another additional optional step in the method, and one that is preferred, is to remove the cleaning solution from the surface by rinsing the surface with a rinsing solution, such as an aqueous solution, with or without the application of acoustic energy to the rinsing solution while the surface is being rinsed. In this context acoustic energy means acoustic energy of any appropriate frequency, such as ultrasonic energy or megasonic energy.

Generally, the surface of the substrate has a plurality of particles adhered to it and at least some of the particles are carried away from the surface when the cleaning solution is removed from the surface, such as by rinsing. In a particularly useful application, the particles are submicron particles, meaning that the particles are smaller than one micrometer. In another particularly useful application, the surface of the substrate has at least one electronic feature having a dimension of less than 0.3 micrometers formed on it. Examples of such electronic features are the fine patterns on semiconductor wafers, such as transistor gates or interconnect lines formed on the surface of a semiconductor wafer. Other examples include the patterns formed in imprint molds, which are the reverse image of the features on a substrate, such as a semiconductor wafer, or the features formed on a photomask that are reduced in the photolithographic process.

Regardless of whether or not the surface of the substrate contains an electronic feature, the cleaning method of the present invention is an isotropic cleaning method that does not utilize a pad to abrasively remove material from the surface of the substrate as is done in a planarization process, such as CMP.

Another embodiment of the present invention is a cleaning solution for cleaning substrates, including semiconductor wafers and other electronic substrates, and that can be used in the method described above. The cleaning solution comprises a cleaning agent, such as a polycarboxylate polymer, or an ethoxylated polyamine, or an ethoxylated quaternized diamine.

Although the present invention has been described in terms of the presently preferred embodiments, it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true scope of the invention.

What is claimed is:

1. A method for removing particles smaller than one micron from the surface of a semiconductor wafer having at least one electronic feature formed on the surface comprising, contacting the surface with a cleaning solution comprised of a polycarboxylate polymer and a base chosen from the group consisting of ammonium hydroxide, TMAH and choline, the cleaning solution having a pH of 8 or higher and not including hydrogen peroxide, and the polycarboxylate polymer having a concentration in the range of 0.01% to 2% by weight.

2. The method of claim 1 wherein the polycarboxylate polymer comprises either homopolymers or copolymers of acrylic acid, methacrylic acid, maleic acid, fumaric acid, or itaconic acid.

3. The method of claim 1 wherein the polycarboxylate polymer comprises a polymer that is prepared from either monomers having the general formula:

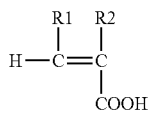

where R1 and R2 is chosen from a hydrogen atom or a methyl radical, or from monomers having the following formula:

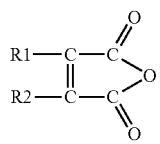

where R1 and R2 are independently H, an alkyl or a phenyl group.

4. The method of claim 1 wherein the polycarboxylate polymer is an acrylic/maleic copolymer.

5. The method of claim 1 wherein the polycarboxylate polymer has an average molecular weight between 300 and 1,000,000 Dalton.

6. The method of claim 1 wherein the polycarboxylate polymer has a concentration in the range of 0.1%-1% by weight.

7. The method of claim 1 wherein the cleaning solution has a pH in the range of 9-12.

8. The method of claim 1 further comprising:

after the surface has been contacted with the cleaning solution, removing the cleaning solution from the surface.

* * * * *